Sept. 28, 1954 E. S. BOERNER Plant Pat. 1,307
CHRYSANTHEMUM PLANT
Filed Oct. 6, 1953
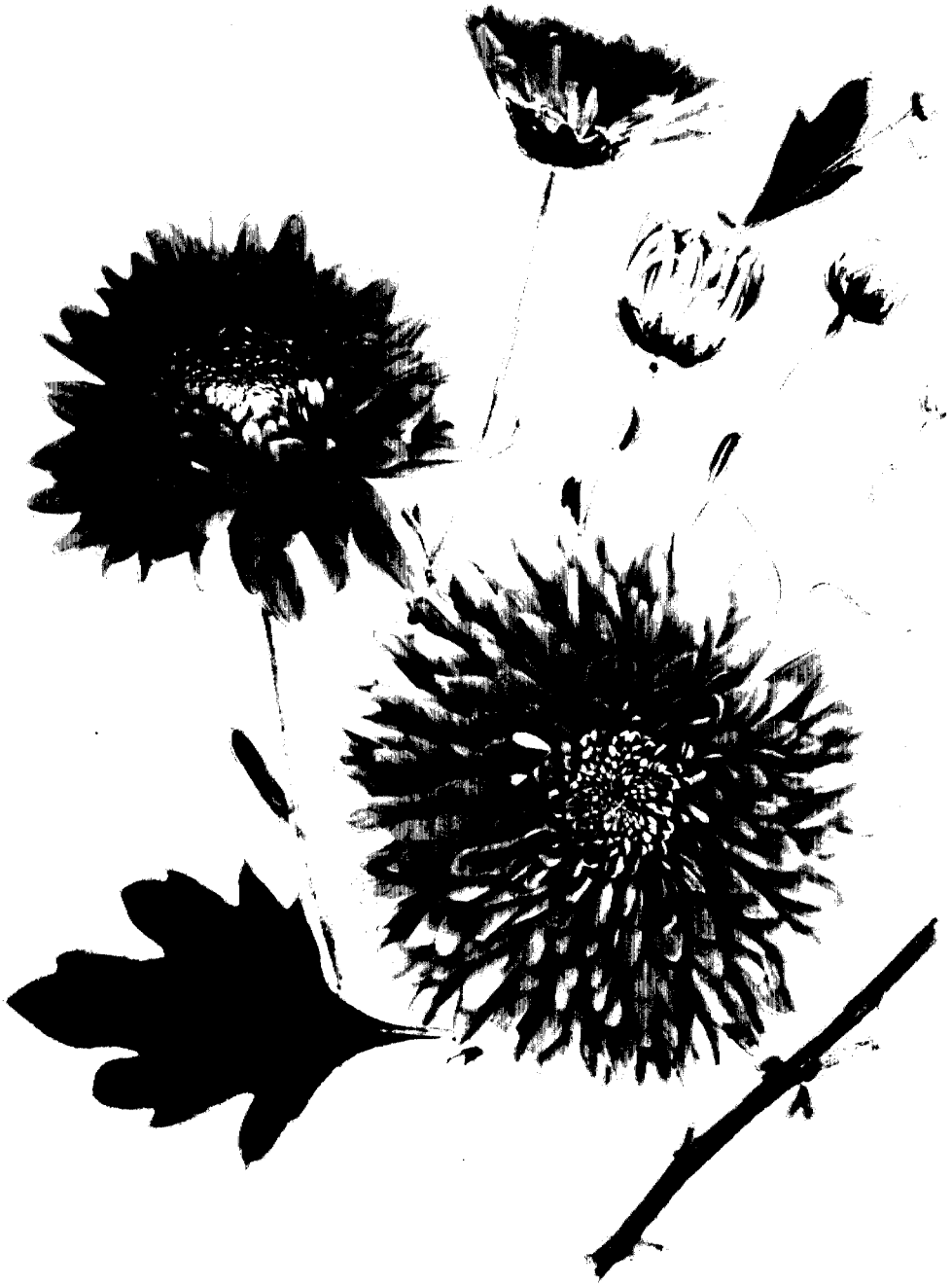
Inventor.
E. S. Boerner
By: Robert Robb
Attorneys.

Patented Sept. 28, 1954

Plant Pat. 1,307

UNITED STATES PATENT OFFICE 1,307

CHRYSANTHEMUM PLANT

Eugene S. Boerner, Newark, N. Y., assignor to Jackson & Perkins Company, Newark, N. Y., a corporation of New York Application October 6, 1953, Serial No. 384,537

1 Claim. (Cl. 47—60)

This invention relates to a new and distinct variety of chrysanthemum plant of the compound dahlia type, which was originated by me by crossing an unnamed and unpatented large-flowered, semi-hardy golden yellow seedling chrysanthemum with another unpatented variety known as "Algonquin," the latter variety being a very early, hardy yellow chrysanthemum.

The primary objective of this breeding was to produce a new variety of chrysanthemum which combines the characteristic large size of the flowers of the semi-hardy seedling parent with the earliness and hardiness characteristics of the variety "Algonquin." In making this cross, numerous seedlings were obtained in a great range of flower colors, of which the present variety was selected as the most desirable and most outstanding, due to its early and very vigorous characteristics, and to its larger flowers than those of the variety "Algonquin," as well as for the distinctive color of the flowers as hereinafter more specifically described.

In addition to the foregoing characteristics, the new variety is notably outstanding for its freedom of bloom and floriferousness, the long-lasting quality of the flowers, particularly on the plants, and the long stems on which the flowers are borne and which make the variety valuable for cut flowers.

These characteristics of the new variety, as aforementioned, altogether definitely distinguish the new variety from its parents, as well as from all other varieties of its class, and asexual reproduction of the new variety by top cuttings and also by underground runners, at Newark, New York, shows that the foregoing characteristics and distinctions come true to form and are established and transmitted through succeeding propagations.

The accompanying drawing shows typical specimens of my new variety, with the flowers, foliage and stems in different stages of development, and depicted in color as nearly true as it is reasonably possible to make the same in a color illustration of this character.

The following is a detailed description of my new variety, as grown and observed in fields at Newark, New York, in the early part of the month of October, and in the early morning, with color terminology in accordance with Ridgway's Color Standards and Nomenclature:

Parentage: An unnamed large-flowered, semi-hardy golden yellow seedling × "Algonquin."

Classification: Compound dahlia type.

Growth: Upright; vigorous and clean; not many suckers.

Cold resistance: Very hardy in northern New York State; flowers very frost resistant as determined by comparison with other varieties grown under comparable cultural conditions.

Blooming period: In Newark, New York climatic area, average date of beginning of bloom is about September 20th, and blooming continues until heavy frosts in October.

Bud:

*Color.*—When sepals first divide — Light Ochraceous Salmon, Plate 15. When petals begin to unfurl—Carmine, Plate 1. When half blown: inside of petals—Carmine, Plate 1, lightly overcast with Nopal Red, Plate 1; reverse of petals—Ochraceous Salmon, Plate 15, lightly overcast with Eugenia Red, Plate 13.

*Peduncle.*—Color—Biscay Green, Plate 17. Strength—strong.

Bloom:

*Size.*—4½ to 5 inches.

*Stems.*—Strong; normal.

*Form.*—Very full, double-thick dahlia type.

*Petalage.*—Very double.

*Color.*—Center of flower—Pompeian Red, Plate 13, slightly overcast with Eugenia Red, Plate 13. Outer petals—Pompeian Red, Plate 13, slightly overcast with Old Rose, Plate 13. Base of petals—Pale Viridine Yellow, Plate 5. Inside of petals—Acajou Red, Plate 13, lightly overcast with Pompeian Red, Plate 13. Reverse of petals—Yellow Ocher, Plate 15, lightly overcast with Pompeian Red, Plate 13.

*Petals.* — Texture — stiff. Form — semi-quilled; ovoid.

*Fragrance.*—Characteristic chrysanthemum.

Plant:

*Form.*—Upright; compact.

*Growth.*—Free.

Foliage:

*Size.*—Small.

*Quantity.*—Normal.

*Texture.*—Soft.

*Color.*—Upper side—Varley's Green, Plate 18. Reverse side—Bice Green, Plate 17.

I claim:

A new and distinct variety of chrysanthemum plant of the very hardy compound dahlia type, substantially as herein shown and described, characterized particularly as to novelty by it freedom and floriferousness of bloom, by its habit of bearing relatively large flowers on relatively long stems, by the distinctive color and long-lasting quality of its flowers, by its early blooming habit, and by the exceptionally good frost resistance of its flowers.

No references cited.